United States Patent [19]

Mandle et al.

[11] Patent Number: 4,678,553

[45] Date of Patent: Jul. 7, 1987

[54] RENATURING REVERSIBLY DENATURED POLYPEPTIDES AND PROTEINS BY ELECTRODIALYSIS OF SOLUTIONS THEREOF IN DENATURANTS

[75] Inventors: Robert J. Mandle, Lexington, Mass.; Wayne A. McRae, Zurich, Switzerland

[73] Assignee: Ionics, Incorporated, Watertown, Mass.

[21] Appl. No.: 884,942

[22] Filed: Jul. 11, 1986

[51] Int. Cl.$^4$ .............................................. B01D 13/02
[52] U.S. Cl. .................................................. 204/182.6
[58] Field of Search .......................... 204/182.6, 301; 210/645, 748; 435/173; 530/343, 344

[56] References Cited

PUBLICATIONS

Neurath et al, The Proteins Chemistry, Biological Activity, and Methods, vol. 1, Part B, pp. 875–884, New York, 1953.

Primary Examiner—John F. Niebling
Assistant Examiner—Ben Hsing
Attorney, Agent, or Firm—Norman E. Saliba

[57] ABSTRACT

A process is disclosed for recovering renatured polypeptides and proteins (collectively "polypeptides") from solution thereof and/or of their S-sulfonate derivatives (collectively "solution of polypeptides") in denaturants comprising:

introducing said solution into a renaturant chamber (compartment, cell, space) of an electrodialysis ("ED") apparatus, said chamber bounded by membranes each of which is substantially permeable to low molecular weight singly charged ions of at least one charge sign and substantially impermeable to said polypeptides and S-sulfonate derivatives, said membranes separating said renaturant chamber from juxtaposed rinsing chambers on each side of the renaturant chamber;

introducing rinsing solutions into said juxtaposed rinsing chambers, said rinsing solutions synergetically with said membranes facilitating a decrease in the chaotropism of said denaturant in said renaturant chamber when a direct electric current is imposed through said renaturant and rinsing chambers in series;

applying a direct electric current (which may have a substantial alternating current component) in series through said juxtaposed renaturant and rinsing chambers in a direction which causes a decrease in the chaotropism of said denaturant in said renaturant chamber thereby decreasing the chaotropism of said denaturant in said solution of polypeptide and/or S-sulfonate derivatives to a chaotropic level which permits substantial refolding of said polypeptides and/or S-sulfonate derivatives, which level is not less than that which results in substantial precipitation of said polypeptide and/or S-sulfonate derivative out of said solution;

maintaining the pH of said solution of polypeptide and/or S-sulfonate derivate at pH's in the range of from about 4 to about 10.

15 Claims, 6 Drawing Figures

RENATURING REVERSIBLY DENATURED POLYPEPTIDES AND PROTEINS BY ELECTRODIALYSIS OF SOLUTIONS THEREOF IN DENATURANTS

BACKGROUND OF THE INVENTION

1. Field of the Invention

It is well known that the information required for the 3-dimensional organization of polypeptides and proteins (herein referred to collectively as "polypeptides"), such as, without limitation, hormones, enzymes, antibodies and virus coats into biologically active structures is present within the amino acid sequence of the polypeptide and if the latter can be placed in a suitable environment the biologically active structures will generally form spontaneously by folding of the amino acid chain(s). The resulting structures are often stabilized by one or more disulfide cross-links formed from sulfhydryl (thio, mercapto) residues in some of the sulfur-bearing amino acids. Unfortunately some biosyntheses, otherwise generally advantageous, result in the production of difficulty soluble aggregates. This is the case, for example, in the production of so-called refractile bodies during biosyntheses by modified E. coli of foot-and-mouth-disease (FMD) virus coat, insulin, some human interferons, human-interleukin 2, porcine-growth-hormone (pGH), urokinase, bovine-growth-hormone (bGH), hepatitus-B-surface-antigen (HBsAg), tissue plasminogen activator (TPA), human-growth-hormone (hGH) and prorennin. Such polypeptide aggregates are often solubilized in aqueous denaturant (chaotropic, lyotropic) solutions (most popularly 4 to 9 molar aqueous solutions of guanidine hydrochloride (guanidinium chloride, "Gu.HCl"), less popularly in solutions of sodium thiocyanate or urea (typically 4 to 9 molar) or in sodium dodecyl sulfate (typically 0.1 to 2.0 percent by weight)) containing typically small amounts of reducing agents, for example sulfhydryl compounds such as beta-mercapto-ethanol ("BME"), dithiothreitol ("DTT") or glutathione ("GSH") to create oxidation-reduction ("redox") potentials sufficient to reduce disulfide links to sulfhydryl residues. In such solutions the polypeptides apparently have little of the structural organization present in the biologically active polymer although the amino acid sequences remain intact.

Biological activity may also be lost from polypeptides (having the correct amino acid sequence for activity) as a result of folding errors introduced during biosynthesis or as a result of the recovery methods used. In such cases it may be desirable to unfold the polypeptides, for example by dissolving them in denaturant solutions generally containing a reducing agent for disulfide links.

In any of the above cases the polypeptide is allowed spontaneously to refold by decreasing the denaturant power (chaotropism, chaotropy) of the chaotropic agent, generally while maintaining conditions under which disulfide links between sulfur bearing amino acids either do not form or (preferably in the case of renatured polypeptides which are stabilized by disulfide links) are in dynamic equilibrium with the precursor amino acid sulfhydryl residues. It is known that the formation of permanent disulfide linkages during the process of refolding may also be inhibited by converting a substantial fraction of the amino acid sulfhydryl and/or disulfide moieties to S-sulfonate groups by reaction of the polypeptide dissolved in chaotropic solution with a sulfite salt and a mild oxidizing agent such as a tetrathionate salt. (The preferred redox potentials for maintaining predominantly S-sulfonate groups are of course different from those potentials which will maintain predominantly sulfhydryl groups.) Following at least partial reduction of the chaotropy and substantial refolding the S-sulfonate groups are removed by reaction with a soluble sulfhydryl compound, preferably in the presence of small amounts of disulfide compound, air, oxygen and/or a mild oxidizing agent.

Decreasing the denaturant power or activity of chaotropic solutions is commonly accomplished by dilution, dialysis or buffer exchange (for example by dialysis against a concentrated solution of a suitable buffer, by diafiltration or by gel permeation chromatography). It is found however that such processes, known in the prior art, used to renature unfolded polypeptide typically result in substantial precipitation of the polypeptide or incorrect refolding thereby reducing substantially the yield of biologically active materials.

It is therefore an objective of this invention to provide processes which result in increased yield of biologically active (renatured) polypeptide from solution in denaturants. This and other objectives will become clear from the brief description of the drawings and description of preferred embodiments herewith.

2. Description of the Prior Art

Electrodialysis ("ED") has become an accepted process and apparatus for transferring ions from one solution to another. The state of the art is well described in pages 726 through 738, Volume 8, Kirk-Othmer Encyclopedia of Chemical Technology, 3d Edition, Wiley, N.Y. 1979. Typically one to several hundred repeating groups of spaced electrolytically conducting membranes are positioned between a single pair of electrodes. Typically in each group of membranes at least one membrane has an electrolytic (Hittorf) transport number for ions of one charge sign substantially different from the transport number of such ions in the solutions to which the ED apparatus is applied. Solutions to be processed are introduced into narrow spaces (compartments, chambers, cells) between the membranes and between the electrodes and the membranes adjacent thereto. A direct electric current (which may have some alternating current component) is applied between the electrodes causing ions to be transferred through the membranes. In the case of ED apparatus operating in a diluting/concentrating mode in which the repeating group comprises two membranes, electrolyte enriched solution is withdrawn from every other compartment (enriching, concentrating, brine, receiving or rinsing compartment) and electrolyte depleted solution from the intervening compartments (depletion, dilution, diluate, dilute, donating, demineralizing, desalting compartments). In the case of ED apparatus operating in a metathesis mode in which the repeating group of membranes comprises three (single decomposition) or four (double decomposition) compartments ions are interchanged among the compartments but the total concentration of electrolyte (expressed in electrical equivalents per unit volume) in each compartment typically remains substantially unaltered.

Ions passing through the above described membranes are accompanied by (electroosmotic) transport of water, typically 4 to 10 moles of water through each membrane per electrical equivalent of ions transferred. Such (specific) water transport through a membrane depends upon the structure of the membrane, on the concentration of electrolyte in the solutions bathing the membrane and upon the current density applied. If the solutions bathing each side of the membrane are both very concentrated then it may be that the ratio of ions to water passing through the membrane is about the same as the ratio in the solution in the compartment donating said ion. In such case ED can result in substantial transfer of solution from the ion donating compartment(s) to the ion receiving compartment(s) without substantial reduction in the concentration of said ions in the nominal donating compartment(s). For example, during ED in desalting mode of a solution originally having about 7 gram-equivalents of Gu.HCl per liter to about 6 gram-equivalents per liter against a rinsing solution having a log-mean concentration of about 0.6 normal, about 70 percent of the volume of the dilution solution was electrolytically transferred to the rinsing stream and about 76 percent of the Gu.HCl, i.e. the solution transferred had a concentration of about 7.3 gram-equivalents per liter. In contrast, during the electrodialysis desalting of a solution originally having about 2 gram-equivalents of Gu.HCl per liter to about 0.33 gram-equivalents per liter (i.e. about 76 percent removal of Gu.HCl) against a rinsing stream having a log-mean concentration of about 0.3, about 50 percent of the volume of the dilution stream was transferred and the solution transferred had a concentration of about 2.7 gram-equivalents per liter.

As mentioned above, ED can also be used in "metathesis" modes in which the ionic composition of a solution can be altered without substantially changing the ionic strength of a solution. For example if a solution of NaCl is introduced to an ED chamber bounded by cation selective ED membranes, Na+ ions can be replaced in part or substantially completely by other cations, the concentration of Cl− anions being substantially unaltered. On the other hand if such NaCl solution is introduced to an ED chamber bounded by anion selective ED membranes Cl− ions can be replaced by other anions without substantially altering the concentration of cations.

It is known in the prior art to decrease the concentration of a solution of a strong denaturing agent and a potentially biologically active polypeptide by adding either water or a buffer to the solution, effectively diluting both denaturant and polypeptides. The method typically results in substantial loss of active polypeptide through precipitation and/or incorrect refolding.

It is also known to decrease the concentration of a strong low molecular weight denaturant in a solution thereof containing potentially active polypeptide by dialysis in which the denaturant diffuses through a semipermeable membrane into water or a buffer. The transfer of polypeptide is inhibited by the membrane. This method also typically results in unsatisfactory yield of biologically active polypeptide.

Diafiltration with either water or a buffer also typically results in unsatisfactory yield of active polypeptide.

DESCRIPTION OF PREFERRED EMBODIMENTS

Figure 1:
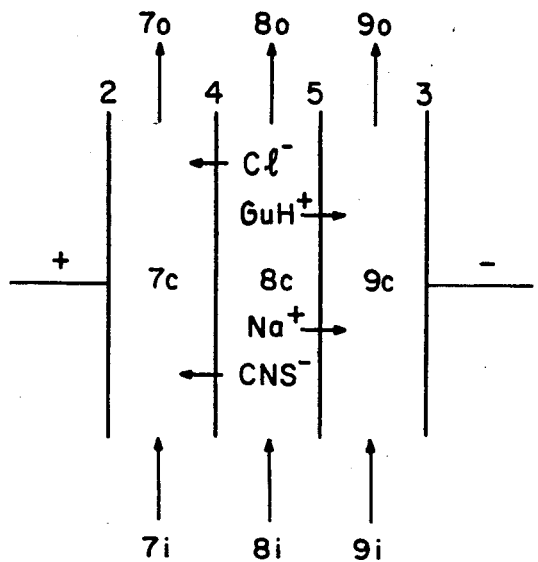
FIG. 1 is a schematic representation of a simple ED apparatus having a single renaturant compartment for carrying out this invention.

In the broadest aspect, the present invention comprises a process for recovering renatured polypeptides (including proteins) from their solutions in reversible denaturants or from solutions of the S-sulfonate derivatives of such polypeptides (collectively "solutions of polypeptides") in such denaturants, which process comprises:

introducing said solution into one or more renaturant compartments (chambers, cells, spaces) of an electrodialysis ("ED") apparatus, each said renaturant compartment separated from adjacent rinsing compartments on each side thereof by membranes which are substantially impermeable to said polypeptides and S-sulfonate derivatives (collectively "polypeptides") but permeable to at least one low molecular weight ion species, preferably at least one of said ion-permeable membranes having a Hittorf transport number for said ion species differing substantially from that of said solution; introducing second aqueous solutions into the rinsing compartments on each side of said renaturant compartment, said second solutions in synergism with said ion-permeable membranes facilitating the reduction of the chaotropy (lyotropy, denaturing power, denaturant activity) of said denaturant in said solution of polypeptide and/or S-sulfonate derivative when a direct electric current is imposed in a chaotropy reduction direction through said renaturant compartment and adjacent rinsing compartments;

passing a direct electric current (which may optionally have a substantial alternating current component) through said renaturant compartment and adjacent rinsing compartments in a direction to reduce the chaotropic activity of said denaturant in said solution of polypeptides and/or their S-sulfonate derivatives, thereby reducing said activity to a reduced activity which is substantially less denaturing but which is not less than the chaotropic activity which would result in substantial precipitation of said polypeptides and/or S-sulfonate derivatives at pH's in the isoelectric range of from about 4 to about 10, which pH's do not substantially decrease the solubility of said polypeptide and/or S-sulfonate derivative in said reduced activity denaturant;

preferably controlling the pH of said solution of polypeptides and/or S-sulfonate derivatives during ED at pH's selected from the range of from about 4 to about 10 which pH's are characterized by not substantially decreasing the solubility of said polypeptides and/or S-sulfonate derivatives in said reduced activity of denaturant;

optionally, when said renatured polypeptide is stabilized by disulfide bonds, controlling the oxidation-reduction potential of said solution of polypeptides and/or S-sulfonate derivatives during ED in the range which is characterized by having a potential which prevents substantial formation of disulfide linkages among sulfur-bearing amino acids;

removing from said renaturant compartment a solution of said polypeptides and/or S-sulfonate derivatives having a substantially reduced activity of denaturant.

Although it is not intended that this invention should be limited by any theory, it appears that the following interpretation may explain the utility of the present invention compared to processes available in the prior art:

Strongly denaturing or chaotropic agents (such as preferably guanidine hydrochloride or other guanidine hydrohalides in the concentration range of from about 4 to about 9 molar, less preferably sodium thiocyanate or other alkali metal thiocyanates, ammonium thiocyanate, quaternary ammonium thiocyanates or urea in the same concentration range, still less preferably detergents such as sodium dodecyl sulfate or other alkali metal aliphatic sulfates in the concentration range of from about 0.01 to about 2 percent and, in the case of polypeptides having disulfide links, preferably with the addition of agents which reversibly sever disulfide bonds between sulfur-bearing amino acids) lead to loss of binding between polypeptide chains in agglomerates or refractile bodies and to loss of tertiary and generally secondary three-dimensional structure within individual polypeptide molecules. Reversibly severing disulfide links, for example by forming sulfhydryl or S-sulfonate residues appears to be important for later stabilization by disulfide links of some renatured, i.e. biologically active refolded polypeptides;

If the strongly denaturating agent is slowly and/or partially removed, while preventing wholesale formation of disulfide links between sulfur-bearing amino acids, then an opportunity may be presented for reorganization, i.e. refolding of the individual polypeptide molecules into biologically active, i.e. substantially native three-dimensional structures. An environment must apparently be selected for such refolding in which the desired biologically active molecular structure has the lowest thermodynamic free-energy of all refolded structures which are reasonably possible kinetically. It appears that other non-native structures in such environment may sometimes have free energies lower than an unfolded polypeptide. Further it may be that the structure of the polypeptide may have to pass through one or more energetically possible intermediate structures to reach the final, biologically active structure. Therefore it appears that the refolding environment must not force an essentially instantaneous "choice" of structure and must remain at least mildly denaturing, i.e. simultaneously renaturing-denaturing, that is the reasonably possible secondary and tertiary structures must remain somewhat labile, hopefully only the biologically active structure being stable. It may also be, in the case of some polypeptides, that the intermediate structures which may have to be passed through on the way to the biologically active final structure are more likely if disulfide links can be temporarily formed. If such is the case then the redox potential of the environment should neither favor only disulfide links or the complete absence of such links;

It appears that the methods known in the prior art for reducing the concentration of strongly denaturing agents may lead at least in part to local environments which force an essentially instantaneous choice of structures, such structures being biologically less than totally active or being agglomerates among several polypeptide molecules which eventually precipitate. In the case of batch dialysis such unfavorable environment may occur at, at least, some point in time in the concentration gradient existing at or near the semipermeable dialysis membrane. In the case of continuous dialysis the unfavorable environments may exist at some region along the dialysis flow path. (It is well-known that very small particles are more soluble than larger particles. Hence it is speculated that particles of optical size formed in a local unfavorable environment may be difficult to redisperse in the average environment and will tend to grow at the expense of dispersed polypeptide if the average environment, as it must for refolding, favors bonding among amino acid residues.) Such temporal and/or spatial unfavorable environments may also be present, for example, at the sites of mixing in the dilution and diafiltration processes known in the prior art, leading to incorrect folding irreversible in the average environment or to precipitation;

On the other hand ED involves not a positive addition of solvent but a positive alteration of electrolyte concentration and/or composition and may therefore minimize or even avoid the formation of regions having unfavorable environments, particularly at applied electric currents which are substantially less than currents which would result in concentration polarization at the membranes. (ED is known to be more "gentle" to polypeptides than other processes for demineralization of polypeptides, e.g. cheese whey, blood plasma, etc.)

It will be clear from the above interpretation that refolding to biologically active structures may be sensitive to the concentrations of renaturing-denaturing agent, to the redox potential and to the time available for refolding of intermediates, unfolding of such and refolding of final structures as well as to other factors in the environment. Such other factors include the pH which must be such as does not lead to electric charges on the polypeptide which inhibit refolding of either the intermediates on the path to the biologically active form or which inhibit refolding of the active structure. The pH must also not encourage stable incorrect refolding or agglomeration.

The concentration of polypeptide in the renaturing-denaturing solution is also likely to be important since the appropriate environment must encourage labile associations between amino acid residues within the polypeptide molecules. At too high concentrations of polypeptide in some environments associations between individual polypeptide molecules can apparently compete with associations within such molecules leading in some cases to agglomeration and precipitation.

Finally the molecular weight, amino acid sequence and composition, presence of non-amino acid residues and of branches in the polypeptides will be important to the specification of preferred environments and times for refolding. Some biologically active polypeptides do not appear to have and/or require disulfide links to stabilize the active structures. Some appear to have little tertiary structure; in still others tertiary structures including domain structures appear to be necessary to confer biological activity.

There are perhaps hundreds of biologically active polypeptides which are of pharmaceutical, industrial and agricultural importance, differing widely in their chemical properties. It is impossible to test the present invention on all of them. Nevertheless although the invention may turn out to be inapplicable in some cases it is believed to be generally applicable to most important polypeptides with obvious variations within the capabilities of those skilled in the art. Examples of application of the process are given herein but they should not be taken as quantitative recipes for application of the process to other polypeptides, i.e. because of the wide diversity of polypeptides, the description of the invention and the examples constitute guidelines for those skilled in the art to apply the invention in other cases.

Referring to FIG. 1 there is indicated schematically a simple ED apparatus which may be applied in either the desalting or metathesis mode comprising anode means 2 and cathode means 3 spaced apart. Between said anode and cathode means there is indicated a renaturant chamber, compartment, cell or space 8c defined by a pair of parallel, spaced apart electrolytically conducting membranes 4 and 5 oriented substantially parallel to said anode and cathode means. Although the figure indicates a vertical, planar configuration of the electrode means and the membranes, the directional orientation is not generally important and there are sometimes advantages for the membranes and electrodes to be monotonically curved or dished i.e. to the minor sections of cylinders. The barriers should be substantially impermeable to the polypeptide of interest or to its S-sulfonate derivative. Typically in the desalting or diluting mode (shown in FIG. 1), membrane 4 is highly selective for anions and membrane 5 is cation selective. Typically in the concentrating mode (for example when the denaturant in the non-electrolyte urea and renaturation will be induced by electrolytically introducing a denaturant antagonist such as ammonium sulfate) membrane 4 is highly selective for cations and membrane 5 is anion selective. In the metathesis mode (for example when $Gu.H^+$ cations will be exchanged at least in part for $Na^+$; $Cl^-$ ions in Gu.HCl solution will be replaced at least in part for $SO_4^{--}$ ions; or $CNS^-$ ions in NaCNS solution will be replaced at least in part by $Cl^-$ or $SO_4^{--}$ ions) both membranes typically have the same ion selectivity as will be obvious to those skilled in the ED art.

Generally at least one of the membranes is ion-selective as described above but it is sometimes advantageous to use membranes which are not substantially ion-selective but are substantially impermeable to the polypeptides or their S-sulfonate derivatives.

Anode means 2 and membrane 4 define between them rinsing cell (chamber, compartment, space) 7c which is also an anode or anolyte cell. Cathode means 3 and membrane 5 together define rinsing cell 9c which is also a cathode or catholyte cell. A solution of polypeptide and/or S-sulfonate derivative thereof if denaturant (which in the desalting or metathesis modes should be an electrolyte but which in the concentration mode may be a non-electrolyte) is introduced into renaturant compartment 8c by inlet means 8i and withdrawn through outlet means 8o. (If the renaturant compartment 8c is operated on non-recirculating batch basis inlet and outlet means 8i and 8o can often conveniently be combined into a single aperture.) Appropriate rinsing (and anolyte) solution is introduced into rinsing compartment 7c by inlet means 7i and withdrawn by outlet means 7o. Rinsing (and catholyte) solution is introduced into rinsing compartment 9c by inlet means 9i and withdrawn by outlet means 9o.

Figure 2:
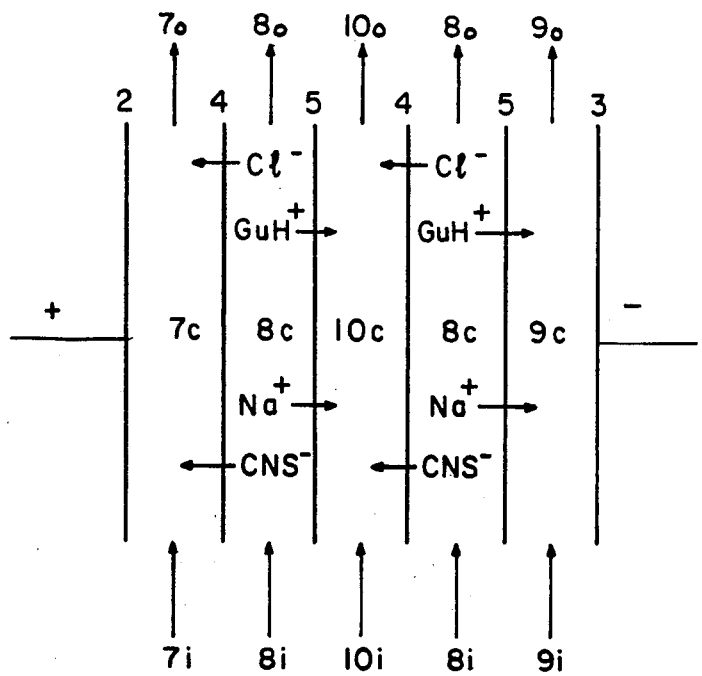
FIG. 2 is a schematic representation of an ED apparatus having two renaturant compartments.

Referring to FIG. 2 there is indicated schematically an ED apparatus comprising two renaturant compartments 8c and differing from the apparatus of FIG. 1 by having a second pair of membranes 4 and 5 and a central rinsing compartment 10c defined between the central pair of membranes. The rinsing solutions introduced into compartments 7c, 9c and 10c may be the same or different. The apparatus may be operated in any of the modes described above by the proper choice of membranes obvious to those skilled in the ED art.

It will be further obvious that additional renaturant compartments can be added between a single pair of electrode means, in each case adding an additional pair of membranes 4 and 5. In commercial ED apparatus, several hundred pairs of membranes (and therefore several hundred pairs of renaturant and rinsing compartments) may be positioned between a single pair of electrode means.

Figure 3:
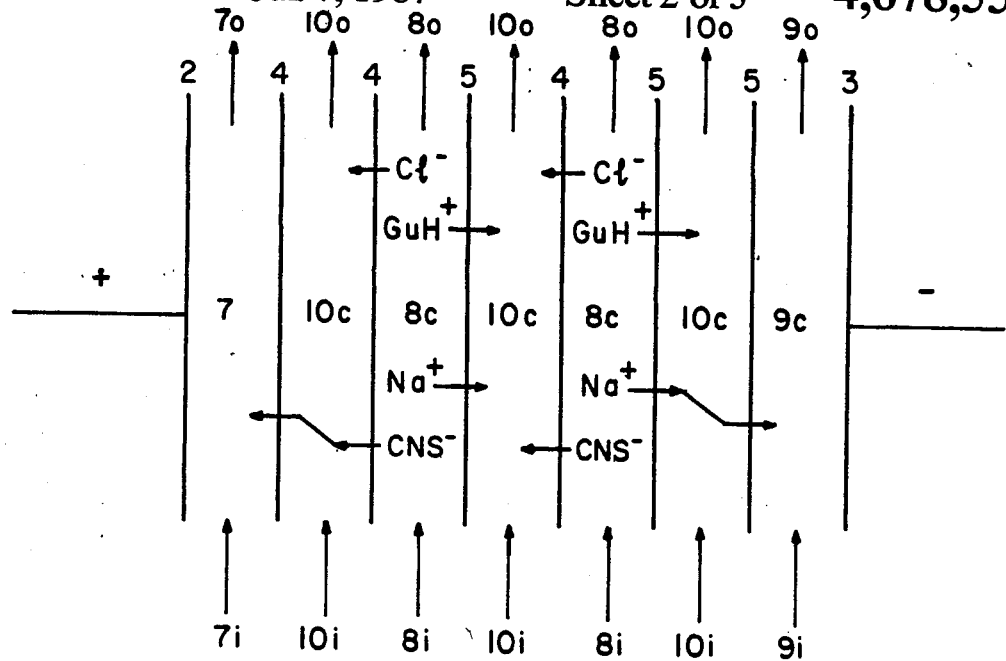
FIG. 3 is a schematic representation of an ED apparatus having two renaturant compartments and buffer cells adjacent to the electrode cells.

Referring to FIG. 3 there is indicated schematically an ED apparatus comprising two renaturant compartments 8c and differing from the apparatus of FIG. 2 by having additional membranes 4 and 5 at the anode means 2 end and cathode means 3 end of the ED apparatus respectively to buffer the interior compartments of the apparatus from the anolyte 7c and catholyte 9c compartments by means of additional rinsing compartments 10c.

The membranes 4 or 5 and electrode means 2 or 3 are typically separated from adjacent membranes or electrodes by distances of 0.5 to 2.0 mm by means of spacer/gaskets which, (if solution is continuously flowed through the compartments defined between said membranes and/or electrodes) generally contain means to mix the solution. The spacer/gaskets may, for example, be fabricated from silicone rubber, chloro-sulfonated polyethylene (e.g. duPont Co. Hypalon A), ethylene-propylene rubber, fluorocarbon elastomers such as vinylidene fluoride-hexafluoropropylene copolymer (e.g. 3M Co. Fluorel, duPont Co. Viton A), vinylidene fluoride-hexafluoropropylene-tetrafluoroethylene terpolymer (e.g. duPont Viton B or G), vinylidene fluoride-tetrafluoroethylene-perfluoro methyl vinyl ether terpolymer (e.g. Viton GLT), tetrafluoroethylene-perfluoromethyl vinyl ether copolymer (e.g. duPont Kalrez) and vinylidene fluoride-chloro-trifluoro ethylene copolymer (e.g. 3M Co. Kel-F 3700); styrene-butadiene or styrene-isoprene thermoplastic block copolymer elastomers (such as Shell International Petroleum Co. Kraton 1101 or 1107), segmented copolyester-ether thermoplastic elastomers (such as duPont Hytrel); polyethylene, polypropylene, polybutylene, plasticized polyvinyl chloride and the like. Particularly suitable are those of the above materials which have low nonspecific absorption of polypeptides which may in some cases be important at reduced chaotropism.

The anode and cathode means may take the form, for example, of sheets, expanded sheets, perforated sheets, perforated and corrugated sheets, woven mesh, wires and the like. The materials of construction of the anode and cathode means may be any material well-known in the art, for example, graphite, nickel, austenitic stainless steels (e.g. type 316), Incoloy 825, Hastelloy C-276, Inconel 600 or titanium, zirconium, niobium or tantalum or their alloys (e.g. Grade VII titanium) coated or plated with one or more platinum group metals and/or oxides thereof.

It is generally preferred that at least one of the membranes 4 and 5 be ion-selective as described above. In some cases at low activity of denaturant certain polypeptides and/or their S-sulfonate derivatives can be more or less irreversibly non-specifically absorbed on some anion-selective membranes. In such case, in the desalting mode for example, the membrane 4 can be substantially non-ion-selective (but electrolytically conductive) and the membrane 5 cation-selective.

In some applications of this invention in the desalting mode it may be desirable for the membrane 4 to be non-ion-selective and the membrane 5 to be cation selective, for example when it is desired to remove sodium dodecylsulfate which has a bulky anion.

In other applications of this invention as described above it may be advantageous to replace part of the guanidinium cation ("Gu.H+") in concentrated solutions of Gu.HCl with a less chaotropic cation such as sodium (Na+), potassium (K+), ammonium, quaternary ammonium and the like or to remove part of the Gu.HCl by ED in the desalting mode and replace at least part of the remaining Gu.H+ with such less chaotropic cation. In this case both membranes defining the renaturant compartments should be cation selective and the rinsing compartments on the anode means side of each renaturant compartment should contain a suitable concentration of Na+ (or other appropriate) cations.

Figure 4:
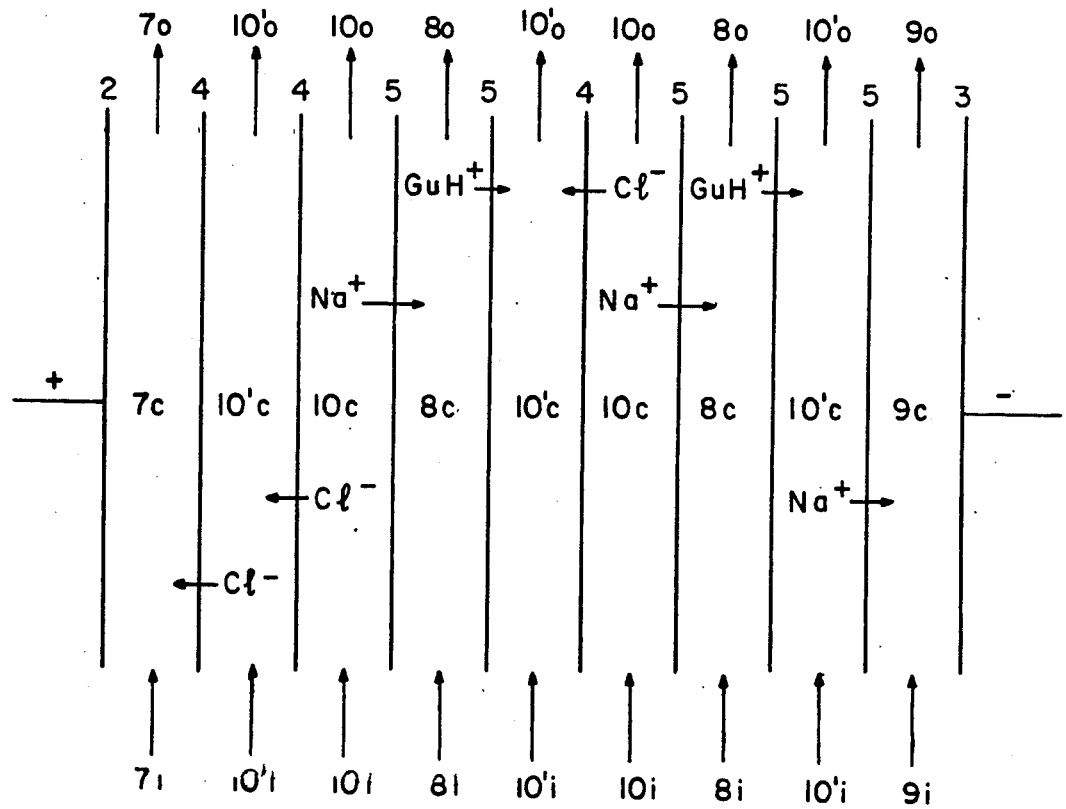
FIG. 4 is a schematic representation of an ED apparatus in the metathesis mode for carrying out cation exchange.

Referring to FIG. 4, if such an ED apparatus contains more than one renaturant compartment then it is desirable to use an ED apparatus more suitable for electrometathesis well known in the art and for example having repeating units of three compartments (rinsing compartments 10c which donate Na+ or other suitable cations to the renaturant compartments 8c and rinsing compartments 10'c which receive Gu.H+) formed from repeating groups consisting of two cation selective membranes 5 and one anion selective membrane 4 as shown schematically in FIG. 4. (Rinsing compartment 10'c adjacent to compartment 7c of course does not receive Gu.H+.)

Figure 5:
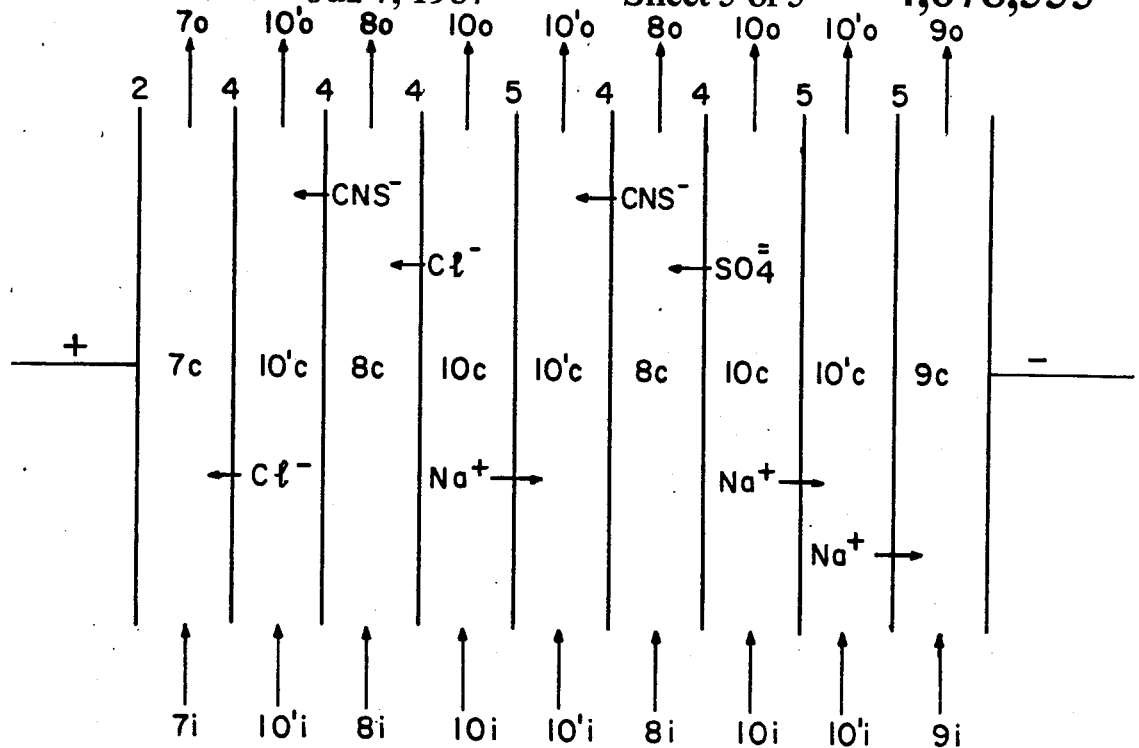
FIG. 5 is a schematic representation of an ED apparatus in the metathesis mode of carrying out anion exchange.
Figure 6:
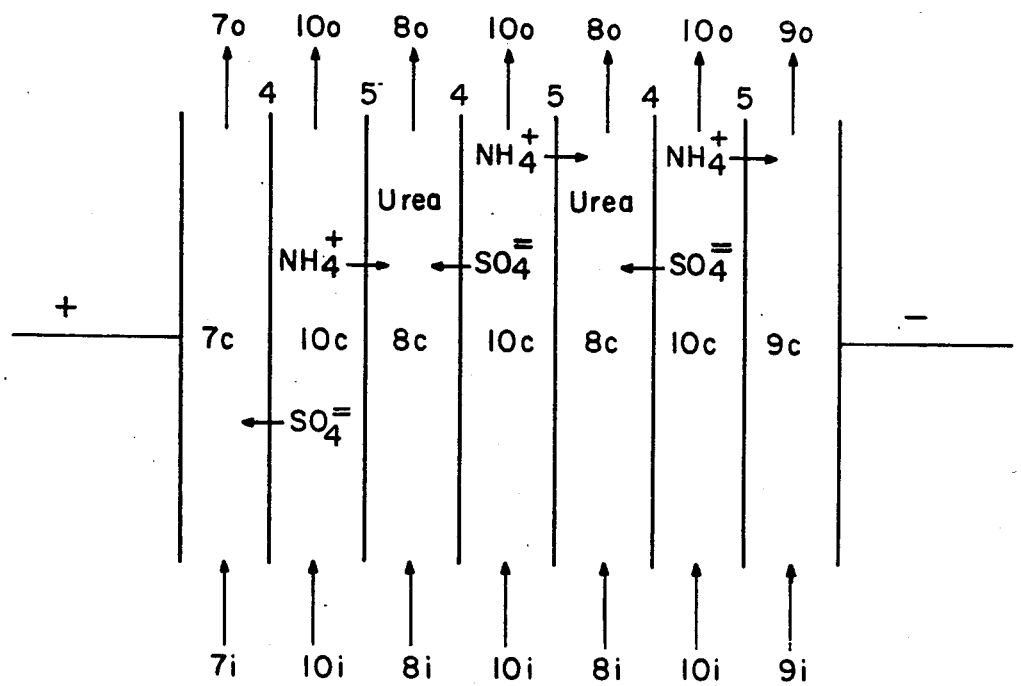
FIG. 6 is a schematic representation of an ED apparatus in the concentration mode.

It may also be advantageous in some cases to replace at least part of the thiocyanate anion (CNS−) in chaotropic solutions of concentrated sodium thiocyanate (NaCNS) with a less chaotropic anion such as chloride (Cl−) or sulfate (SO4−−) or after removing part of the NaCNS by ED in the desalting mode replacing at least part of the remaining CNS− with Cl− or SO4−−. In such ED anion exchange case both membranes defining the renaturant compartment should be anion selective and the rinsing compartments on the cathode means side of the renaturant compartments should contain an appropriate concentration of Cl−, SO4−− (or other suitable) anions. Referring to FIG. 5, it will be advantageous in this case if more than one renaturant compartment is desired to use an electrometathesis ED apparatus well-known in the art and having, for example, repeating units of three compartments (CNS− receiving, renaturant and Cl− or SO4−− donating) formed from repeating groups consisting of two anion-selective membranes and one cation-selective membrane. Rinsing compartments 10c donate Cl− or SO4−− or other suitable anions to the renaturant compartments 8c and rinsing compartments 10'c receive CNS−. (Sulfate appears to be a particularly powerful renaturing replacement for thiocyanate.) Concentrated (e.g. in excess of 4 molar) solutions of urea are often used as solubilizing denaturants for polypeptides and/or their S-sulfonate derivatives. It is well known that urea is generally not appreciably ionized in such solutions and is a much less powerful denaturant than agents such as Gu.HCl or NaCNS. Polypeptides and their S-sulfonate derivatives reversibly denatured in urea solutions can be renatured by electrodialytically introducing denaturant antagonists such as sodium or ammonium sulfate into the denaturant solution. Referring to FIG. 6, rinsing compartments 10c donate Na+ or other suitable cations and SO4−− or other suitable anions to the renaturant compartments 8c. The apparatus preferably comprises repeating groups consisting of one anion selective and one cation selective membrane. Either ion-selective membrane may be replaced by a substantially non-ion-selective membrane substantially impermeable to the polypeptides and/or S-sulfonate derivatives in the renaturant compartments.

It is believed that the following table approximates the lyotropic (chaotropic, denaturant) series of some electrolytes for polypeptides:

| Cations in Increasing Order of Effectiveness | Anions in Decreasing Order of Effectiveness |
| --- | --- |
| K+ | SCN− |
| NH4+ | I− |
| Na+ | Br− |
| Li+ | Cl− |
| Gu.H+ | NO3− |
|  | SO4= |

Each cation listed appears to form a denaturant electrolyte with the anions at equal or higher levels in the table and "renaturant" electrolytes with anions lower in the table.

Suitable cation-selective membranes include fabric reinforced, homogeneous, isoporous gel membranes comprising sulfonated crosslinked polystyrene, sulfonated crosslinked polyvinyl toluene or crosslinked polysulfoethyl methacrylate (such as type CR61, CR62 and CR63 of Ionics, Incorporated, Watertown, Mass. U.S.A.); fabric reinforced, macroheterogeneous membranes based on cation exchange resins ground to an impalpable powder, mixed with a hydrophobic thermoplastic and sheeted (such as types MC3142 and 3470 of IONAC Chemical Div., Birmingham, N.J., U.S.A.); fabric reinforced microheterogeneous interpolymer membranes (such as type CMV of Asahi Glass Co., Tokyo, Japan and types CL-25T, CM-1, CM-2 and CLE-E of Tokuyama Soda Co., Tokuyama City, Japan); and unreinforced microheterogeneous interpolymer membranes (such as types C-60 and C-100 of AMF Inc., Springdale, Conn., U.S.A.). Particularly preferred are fluorinated membranes (such as the fabric reinforced types 423 and the unreinforced type 117, both of duPont Co., Wilmington, Del., U.S.A. and types C-311, 313 and 322 of AMF Inc.).

Suitable anion selective membranes include fabric reinforced, homogeneous, isoporous gel membranes comprising crosslinked polystyrene containing quaternary ammonium groups or crosslinked, quaternized dimethylaminoethylmethacrylate (such as types AR103 and AR204 of Ionics); fabric reinforced, macroheterogeneous membranes based on anion exchange resins ground to an impalpable powder, mixed with a hydrophobic thermoplastic and sheeted (such as type MA3148 of IONAC Chemical Div.); fabric reinforced microheterogeneous interpolymer membranes (such as type AMV of Asahi Glass Co. and types AM1, AM2 and AM3 of Tokuyama Soda Co.); and unreinforced microheterogeneous membranes (such as types A-60 and A-100 of AMF Inc.). Particularly preferred are antifouling anion-selective membranes (such as type AR204SXZL of Ionics and types AFN and ACLE-5P of Tokuyama Soda); anion-selective membranes having fixed negatively charged groups on the surface (such as type ACS of Tokuyama Soda); and fluorinated anion-selective membranes (such as type TSK of Toyo Soda Manufacturing Co., Yamaguchi, Japan).

Such particularly preferred anion-selective membranes are desirable in those cases when polypeptides and/or their S-sulfonate derivatives are more or less irreversibly non-specifically absorbed on other anion-selective membranes, particularly at low concentrations of denaturant.

Suitable non-ion-selective membranes include fabric reinforced ultrafiltration membranes having pore sizes in the range of from about 2 to about 20 nanometers and based for example on cellulose acetate, polyamides, polysulfones or vinyl chloride-acrylonitrile copolymers and which are not substantially swollen in strongly denaturing electrolytes. Particularly suitable are ultrafiltration membranes based on polyvinylidene fluoride or on lightly sulfonated polysulfone.

EXAMPLE 1

One liter of aqueous solution is prepared having a pH of about 7 and containing about 670 grams guanidine hydrochloride ("Gu.HCl", Molecular Weight about 95.5), about 4.7 grams phosphate as a buffer, about 0.4 grams of the tetrasodium salt of ethylenediamine-tetraacetic acid ("EDTA"), about 1.2 grams 2-mercaptoethanol ("BME", to maintain the oxidation-reduction potential of the solution in a range in which most of the sulfur-bearing amino acids are in the sulfhydryl form rather than the disulfide form) and about 30 grams crude Foot-and-Mouth-Disease ("FMD") capsid polypeptide (of which about half is available FMD polypeptide). The solution is chromatographed on buffered Sephacryl S-300 (Pharmacia Fine Chemicals, Uppsala, Sweden) according to the manufacturer's recommendations well-known in the art, and an intermediate fraction of about 200 ml of solution is recovered containing substantially all of the available FMD polypeptide. This latter solution is recycled on a batch basis through a Medimat ®110 ED stack (Ionics Incorporated, Watertown, Mass., U.S.A.) having 4 renaturing (diluting) compartments, each with an effective area of about 110 $cm^2$ and a thickness of about 0.1 cm. The membranes are Ionics' AR103QZL and CR61CZL equilibrated in a polypeptide-free solution of Gu.HCl, EDTA and BME otherwise as described above. The superficial velocity of the polypeptide solution in the renaturant (diluting) compartments of the ED stack is about 10 cm/sec. Care is taken to exclude air from the recirculating polypeptide solution by blanketing the surface of the solution in the covered batch reservoir with oxygen-free-nitrogen gas ("OFN"). A solution containing about 190 grams Gu.HCl per liter is recirculated through the rinsing (receiving) compartments, the flow rate thereof carefully adjusted to maintain the average pressure in the rinsing compartments about 10 cm of water greater than the average in the regenerant compartments to minimize loss of polypeptide through cross-leaks. Platinum foil probes are inserted in the compartment adjacent to the electrode compartments. A direct electric current of about 3.5 amperes is applied initially to the ED stack and thereafter the current is adjusted to maintain at approximately a constant value (about 7 to 9 volts) the potential initially measured between the platinum probes. The volume of the recirculating polypeptide solution is maintained approximately constant by the frequent addition of a deaerated, cold solution having a pH adjusted to about 8.3 and containing per liter about 480 grams urea (Molecular Weight about 60, a renaturing-denaturing non-electrolyte), about 1.7 grams 2-amino-2-hydroxy-methyl-1,3-propanediol ("Tris", to maintain the pH of the resulting urea containing polypeptide solution in a range in which substantial precipitation of the polypeptide does not occur) and about 1.2 grams BME (to maintain the redox potential of the solution in a range in which most of the sulfur-bearing amino acids are in the sulfhydryl form rather than the disulfide form). ED is continued until the electrical conductivity of the recirculating polypeptide solution reaches an apparent steady-state value. The temperature of the polypeptide solution is controlled at about 4° C. by passing both the recirculating polypeptide and rinsing solutions through heat exchangers cooled with ice water. The resulting polypeptide solution is adjusted to about pH 10 with sodium hydroxide and passed through a buffered DE52 type diethylaminoethyl ("DEAE") cellulose anion-exchange column following the manufacturer's instructions, well-known in the art. The effluent polypeptide solution is aerated for several hours at 4° C. with filtered air to oxidize most of the BME (thereby slowly moving the redox potential to a range in which sulfer-bearing amino acids can form disulfide links, tending to stabilize the folded structure of the polypeptide). The FMD polypeptide is shown to be biologically active by its reactivity with FMD antiserum and to have been recovered in high yield. Substantially urea free polypeptide may be recovered by diafiltration, preferably first with buffered but dilute urea solution and finally with sterile water.

EXAMPLE 2

The procedure of Example 1 is repeated except tht after the crude FMD capsid solution is chromatographed on buffered Sephacryl S-300, it is recycled on a batch basis through a Medimat 110 ED stack in the metathesis mode having four repeating groups of three membranes each (two AR103QZL anion-selective membranes and one CR61CZL cation-selective membrane). A concentrated solution of ammonium sulfate is recirculated through the rinsing compartments (each defined between an anion and a cation selective membrane) and the FMD capsid solution in Gu.HCl through the regenerant compartment (defined by two anion-selective membranes). The flow velocity in the regenerant compartments is about 10 cm/sec. The velocity through the rinsing compartment is adjusted to maintain the average pressure in the rinsing compartments about 10 cm of water greater than the average in the regenerant compartments to minimize loss of polypeptide through cross-leaks. A direct electric current of about 3.5 amperes is applied. Care is taken to exclude air from the recirculating polypeptide solution. ED is terminated before turbidity appears in the polypeptide solution (determined by preliminary tests) and the resulting polypeptide solution worked up as described in Example 1. The FMD polypeptide is shown to be biologically active. Substantially guanidine free polypeptides may be recovered by diafiltration.

EXAMPLE 3

One liter of aqueous solution is prepared having a pH of about 8.8 and containing about 670 grams Gu.HCl, about 6 grams Tris, about 0.4 grams EDTA, about 7.8 grams BME and crude porcine growth hormone ("pGH") having about 15 to 20 grams potentially available active pGH. The solution is chromatographed on Sephacryl S-300. The recovered fractions containing substantial pGH are combined and electrodialyzed as described in Example 1, the volume of the polypeptide solution being maintained by frequent addition of solution having a pH of about 9 and containing in each liter about 1.8 grams Tris, about 3.9 grams BME and about 420 grams urea. After apparent steady state conductivity is reached, the pH of the resulting polypeptide solution is adjusted to about 7 with hydrochloric acid and the solution is passed through buffered DE52 DEAE cellulose anion-exchange column, following the manufacturer's instructions, well-known in the art. The pH of the effluent polypeptide solution is adjusted to about 10 with sodium hydroxide solution. The resulting solution is aerated for several hours at 4° C. with filtered air. A high yield of biologically active pGH is obtained. Substantially urea-free polypeptide may be obtained by dialysis and/or diafiltration as well-known in the art, preferably first with buffered dilute urea solution and finally with sterile water.

EXAMPLE 4

One liter of aqueous solution is prepared having a pH of about 8 and containing about 575 grams Gu.HCl, and about 6 grams of Tris and also containing crude prorennin having about 8 to 10 grams potentially active pro-rennin. The polypeptide is S-sulfonated by adding with stirring about 20 grams of sodium sulfite and 10 grams of sodium tetrathionate from concentrated, freshly prepared solutions of each. After about 4 hours the resulting solution is electrodialyzed as described in Example 1. The volume of the polypeptide solution is maintained by periodically adding a cold solution having a pH of about 7.5 and containing per liter about 300 grams urea and about 6 grams of Tris. The electroldialysis is continued until the polypeptide S-sulfonate solution has a substantially stable electrolytic conductivity. The resulting solution is loaded on a suitably buffered type DE52 DEAE cellulose column according to the manufacturer's recommendations well-known in the art. The column is rinsed and eluted with a 0 to 0.15 Molar sodium chloride gradient, prorennin polypeptide eluting in the vicinity of 0.07 Molar sodium chloride. The eluted prorennin is diafiltered against a solution containing per liter about 300 grams urea and about 8 grams of the hydrochloride salt of Tris. About 0.3 grams per liter of glutathione and 0.03 grams of the disulfide thereof are added. After about 15 hours at room temperature the resulting solution is dialyzed against a solution having a pH of about 8 containing about 6 grams per liter of Tris. After autocatalytic activation the contained protein was found to be highly active in a standard milk coagulation test.

EXAMPLE 5

One liter of aqueous solution is prepared having a pH of 8.3 and containing about 480 grams urea, about 17 grams Tris, about 8 grams BME and about 30 grams crude FMD capsid polypeptide. The solution is chromatographed on buffered DE52 DEAE cellulose following the manufacturer's instructions, well known in the art. The clear fraction of the effluent is recycled on a batch basis through the renaturant (concentrate) compartments of a Medimat ®110 ED stack operating in the concentrating mode having 4 renaturant (concentrating) compartments. Solution containing concentrated ammonium sulfate is recirculated through the rinsing (diluting) compartments. A current of about 3.5 amperes is applied. The solutions are recirculated at a velocity of about 10 cm/sec. ED is terminated before turbidity appears in the polypeptide solution (determined by preliminary tests). The resulting polypeptide solution is removed from the ED apparatus and is aerated for several hours at 4° C. with filtered air to oxidize most of the BME (thereby slowly moving the redox potential to a range in which sulfur-bearing amino acids can form disulfide links tending to stabilize the folded structure of the polypeptide). The FMD polypeptide is shown to be biologically active. Substantially urea-free polypeptide may be recovered by dialysis, first against buffered dilute urea solution and then against sterile water.

It will be apparent to those skilled in the arts that numerous changes and modifications may be made in the preferred embodiments of the invention described above without departing from the scope of the invention. Accordingly, the whole of the foregoing description is to be construed in an illustrative and not in a limitative sense, the scope of the invention being defined solely by the appended claims.

What is claimed is:

1. A process for recovering at least one substantially renatured polypeptide from a solution of said polypeptide and/or its S-sulfonate derivative reversibly denatured in aqueous denaturant, said process comprising:

(a) introducing said solution of said polypeptide and/or its S-sulfonate derivative into at least one renaturant compartment of an electrodialysis apparatus, said compartment defined by membranes each of which is substantially permeable to low molecular weight singly charged ions of at least one charge sign and substantially impermeable to said polypeptides and S-sulfonate derivatives, said membranes also defining rinsing compartments juxtaposed on each side of said renaturant compartment;

(b) introducing second aqueous solutions into said juxtaposed rinsing compartments, said second solutions adapted in combination with said membranes to permit reduction of the chaotropy of said denaturant in said renaturant compartment upon the application of a direct electric current in at least one of the possible directions through said renaturant compartment and said juxtaposed rinsing compartments in series;

passing a substantially direct electric current in series through said renaturant compartment and said juxtaposed rinsing compartments in a direction to cause reduction of the chaotropy of said denaturant in said renaturant compartment thereby reducing the chaotropy of said denaturant in said solution of polypeptide and/or S-sulfonate derivative to a level characterized by its ability to permit at least partial refolding of such polypeptide and/or S-sulfonate derivative which level is not less than that which would result in substantial precipitation of said polypeptide and/or its S-sulfonate derivatives out of said solution at pH's in the range of from about 4 to about 10, which pH's do not substantially decrease the solubility of said polypeptide and/or S-sulfonate derivative at said chaotropy level;

(d) maintaining the pH of said solution of polypeptide and/or S-sulfonate derivative during electrodialysis at pH's in the range of from about 4 to about 10 which pH's are characterized by not substantially decreasing the solubility of said polypeptide and/or S-sulfonate derivatives at said reduced chaotropy level; and (e) removing from said renaturant compartment a solution of said polypeptide and/or S-sulfonate derivative having a substantially reduced chaotropy level.

2. A process according to claim 1 in which the redox potential of said solution of polypeptide and/or S-sulfonate derivatives during electrodialysis is maintained in a range which range has the property of substantially inhibiting formation of disulfide linkages by sulfur bearing amino acids of said polypeptide and/or S-sulfonate derivative.

3. A process according to claim 1 in which said denaturant comprises at least in part an electrolyte and in which said direct electric current causes a substantial reduction in the concentration of said electrolyte in said solution of polypeptide and/or S-sulfonate derivatives thereof.

4. A process according to claim 1 in which said denaturant comprises at least in part an electrolyte, said direct electric current causes a substantial reduction in the concentration of said electrolyte in said solution of polypeptide and/or S-sulfonate derivative and in which a non-electrolyte denaturant is added to said solution of polypeptide and/or S-sulfonate derivatives.

5. A process according to claim 1 in which said denaturant comprises at least in part an electrolyte, said direct electric current causes a substantial reduction in the concentration of at least one ion of said electrolyte in said solution of polypeptide and/or S-sulfonate derivatives thereby reducing the chaotropy of said denaturant in said solution of polypeptide and/or S-sulfonate derivatives.

6. A process according to claim 1 in which said direct electric current causes a substantial increase in the concentration of electrolyte in said solution of polypeptide and/or S-sulfonate derivatives which electrolyte is characterized by reducing the chaotropism of said denaturant in said solution of polypeptide and/or S-sulfonate derivatives.

7. A process according to claim 1 in which said denaturant comprises at least in part an electrolyte selected from the group consisting of guanidinium halides, the alkali metal salts of thiocyanate, ammonium thiocyanate, the quaternary ammonium salts of thiocyanate and the alkali metal salts of dodecyl sulfate and in which said direct electric current causes a substantial reduction in the concentration of said electrolyte in said solution of polypeptide and/or S-sulfonate derivatives thereof.

8. A process according to claim 1 in which said denaturant comprises at least in part an elctrolyte selected from the group consisting of guanidinium halides, the alkali metal salts of thiocyanic acid, ammonium thiocyanate, quaternary ammonium salts of thiocyanic acid and the alkali metal salts of dodecyl sulfate in which said direct electric current causes a substantial reduction in the concentration of said electrolyte in said solution of polypeptide and/or S-sulfoante derivative and in which urea is added to said solution of polypeptide and/or S-sulfonate derivative.

9. A process according to claim 1 in which said denaturant comprises at least in part an electrolyte selected from the group consisting of guanidinium halides, the alkali metal salts of thiocyanate anion, ammonium thiocyanate, quaternary ammonium salts of thiocyanate anion and the alkali metal salts of dodecylsulfuric acid, and in which said direct electric current causes a substantial reduction in the concentration of at least one ion of said electrolyte in said solution of polypeptide and/or S-sulfonate derivatives thereby reducing the denaturant activity of said denaturant in said solution of polypeptide and/or S-sulfonate derivatives.

10. A process according to claim 1 in which said denaturant comprises at least in part an electrolyte selected from the group consisting of guanidine hydrohalides, the alkali metal thiocyanates, ammonium thiocyanate, quaternary ammonium thiocyanates, and the alkali metal dodecyl sulfates, and in which said direct electric current causes a substantial replacement of at least one ion of said electrolyte in said solution of polypeptide and/or S-sulfonate derivatives by ions of like charge thereby reducing the denaturant activity of said denaturant in said solution of polypeptide and/or S-sulfonate derivatives.

11. A process according to claim 1 in which said denaturant comprises at least in part guanidinium chloride, and in which said direct electric current causes a substantial replacement of guanidium cation in said solution of polypeptide and/or S-sulfonate derivatives by cations selected from the group consisting of alkali metal cations, ammonium and quaternary ammonium cations.

12. A process according to claim 1 in which said denaturant comprises at least in part guanidinium chloride, and in which said direct electric current causes a substantial replacement of chloride in said solution of polypeptide and/or S-sulfonate derivatives by sulfate anion.

13. A process according to claim 1 in which said denaturant comprises at least in part sodium thiocyanate, and in which said direct electric current causes a substantial replacement of thiocyanate anion in said solution of polypeptide and/or S-sulfonate derivatives by anions selected from the group consisting of halide and sulfate anions.

14. A process according to claim 1 in which said denaturant is urea and in which said direct electric current causes an increase in said solution of polypeptide and/or S-sulfonate derivatives of electrolyte selected from the group consisting of the sulfates of the alkali metals and ammonium.

15. A process for recovering at least one substantially renatured polypeptide from a solution of said polypeptide and/or its S-sulfonate derivative reversibly denatured in aqueous denaturant of which at least part is an electrolyte, said process comprising:

(a) introducing said solution of said polypeptide and/or its S-sulfonate derivative into at least one renaturant compartment of an ED apparatus, said compartment defined by membranes which are substantially permeable to low molecular weight singly charged ions of at least one charge sign and substantially impermeable to said polypeptides and S-sulfonate derivatives, said membranes also defining rinsing compartments juxtaposed on each side of said renaturant compartment;

(b) introducing second aqueous solutions into said juxtaposed rinsing compartments, said second solutions in combination with said membranes permitting reduction of the chaotropism of said denaturant in said renaturant compartment upon the application of a direct electric current in at least one direction through said renaturant compartment and said juxtaposed rinsing compartments in series;

(c) passing a substantially direct electric current in series through said renaturant compartment and said juxtaposed rinsing compartments in a direction which causes a substantial reduction in the concentration of at least one ion of said electrolyte in said solution of polypeptide and/or S-sulfonate derivatives thereby reducing the chaotropy of said denaturant in said solution of polypeptide and/or S-sulfonate derivatives; and (d) removing from said renaturant compartment a solution of said polypeptide and/or S-sulfonate derivative having a substantially reduced chaotropy level.

* * * * *